United States Patent [19]
Eickhoff et al.

[11] Patent Number: 5,571,536
[45] Date of Patent: Nov. 5, 1996

[54] FORMULATIONS OF COMPOUNDS AS NANOPARTICULATE DISPERSIONS IN DIGESTIBLE OILS OR FATTY ACIDS

[75] Inventors: W. Mark Eickhoff, Downingtown; Karl R. Mueller, Pexton; David A. Engers, Collegeville, all of Pa.

[73] Assignee: Nano Systems L.L.C., Collegeville, Pa.

[21] Appl. No.: 384,057

[22] Filed: Feb. 6, 1995

[51] Int. Cl.⁶ .................................................. A61K 9/14
[52] U.S. Cl. .................... 424/489; 424/450; 424/495; 424/498; 424/499; 514/772.1; 514/951; 514/937; 514/938
[58] Field of Search .................................. 424/489, 450, 424/495, 498, 499; 514/951, 772.1

[56] References Cited

U.S. PATENT DOCUMENTS 5,145,684  9/1992  Liversidge et al. ...................... 424/489
5,430,021  7/1995  Rudnic et al. ............................ 514/14

*Primary Examiner*—Thurman K. Page
*Assistant Examiner*—Sharon Howard
*Attorney, Agent, or Firm*—Rudman & Balogh

[57] ABSTRACT

Nanoparticulate crystalline drug substances formulated in an aqueos phase emulsified in oil, are able to be made at less than 1000 nm size and provide increased bioavailability and lymphatic uptake following oral administration.

3 Claims, No Drawings

FORMULATIONS OF COMPOUNDS AS NANOPARTICULATE DISPERSIONS IN DIGESTIBLE OILS OR FATTY ACIDS

FIELD OF THE INVENTION

The present invention relates to formulations of compounds as nanoparticulate aqueous dispersions emulsified in digestible oils or fatty acids with or without additional stabilizers. More particularly, the present invention increases the bioavailability of phamacological compounds and allows pharmacological compounds to be delivered directly to the lymphatic systems following oral administration.

BACKGROUND OF THE INVENTION

Intestinal lymphatic uptake has long been proposed as a route for drugs to increase systemic bioavailability by avoiding first pass metabolism and hepobiliary elimination pathways following oral administration. However, no strong data in the literature exists which suggest there is an oral delivery system which actually can target this absorption pathway to any great extent. Formulation of drugs in oils and fatty acids is a traditional approach which has shown some success, but is by no means predictable. These approaches have focused on compounds with high log P and high lipid solubility, and even under these conditions results have been mixed. This approach suffers from the limitation that most compounds have limited solubility in digestible oils or fatty acids to the extent that development into a solid dosage form is not practical, that is, too large a capsule is needed to provide the dose.

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm).

The present invention provides improved oral bioavailability for any compound which possesses extensive first pass elimination and that can be formulated as a nanoparticulate in a digestible oil or fatty acid. It is theorized that nanoparticles are rapidly carried intact into the intestinal lymphatic ducts/vessels via the lipid transport pathway where subsequent dissolution in lymph/blood partitioning occurs. Eventually, any undissolved nanoparticulate will drain into the systemic circulation and represent a late phase delivery pathway.

SUMMARY OF THE INVENTION

The present invention provides an orally administratable particle which consists essentially of 0.1–50% by weight of a crystalline drug substance having a solubility in water of less than 10 mg/ml. The drug substance has a non-crosslinked modifier adsorbed on the surface thereof in an amount of 0.1–20% by weight. The particles are suspended in an aqueous phase. The aqueous phase is emulsified in an oil or fatty acid. The particles maintain an effective size of less than 1000 nm.

In a preferred form of the present invention, the oil phase comprises oleic acid.

DESCRIPTION OF THE PREFERRED EMBODIMENT

The present invention is based on the hypothesis that oral bioavailability can be dramatically improved for any compound which possesses extensive first pass elimination and that can be formulated as a nanoparticulate in a digestible oil or fatty acid.

The present invention can be practiced with a wide variety of crystalline materials that are water insoluble or poorly soluble in water. As used herein, poorly soluble means that the material has a solubility in aqueous medium of less than about 10 mg/ml, and preferably of less than about 1 mg/ml. Examples of the preferred crystalline material are as follows. The therapeutic candidates include [6-methoxy- 4-(1-methylethyl)-3-oxo-1,2-benzisothiazol-2-( 3H)-yl] methyl 2,6-dichlorobenzoate, S,S-dioxide, described in U.S. Pat. No. 5,128,339 (WIN 63394), closporin, propanolol, antifungals, antivirals, themetherapeutics, oligonucleotides, peptides or peptidomimetics and proteins. In addition it is believed that vaccines can also be delivered to the lymphatic system by use of the present invention. The present invention also allows imaging of the intestinal lymphatic system with X-ray or MRI agents formulated as nanoparticles in digestible oils or fatty acids. Potential imaging agents include any X-ray or MRI nanoparticulate core.

Suitable surface modifiers can preferably be selected from known organic and inorganic pharmaceutical excipeints. Such excipients include various polymers, low molecular weight oligomers, natural products and surfactants. Preferred surface modifiers include nonionic and ionic surfactants.

Representative examples of surface modifiers include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthlate, microcrystalline cellulose, magnesium aluminum silicate, triethanolamine, polyvinyl alcohol, and polyvinylpyrrolidone (PVP). Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Particularly preferred surface modifiers include polyvinylpyrrolidone, tyloxapol, poloxamers such as Pluronic F68 and F108, which are block copolymers of ethylene oxide and propylene oxide, and polyxamines such as Tetronic 908 (also known as Poloxamine 908). which is a tetrafunctinnal block copolymer derived from sequential addition of propylene oxide and ethylene oxide to ethylenediamine, available from BASF, dextran, lecithin, dialkylesters of sodium sulfosuccinic acid, such as Aerosol OT, which is a dioctyl ester of sodium sulfosuccinic acid, available from American Cyanimid, Duponol P, which is a sodium lauryl sulfate, available from DuPont, Triton X-200, which is an alkyl aryl polyether sulfonate, available from Rohm and Haas, Tween 20 and Tween 80, which are polyoxyethylene sorbitan fatty acid esters, available from ICI Specialty Chemicals: Carbowax 3550 and 934, which are polyethylene glycols available from Union Carbide; Crodesta F-110, which is a mixture of sucrose stearate rid sucrose distearate, available from Croda Inc., Crodesta SL-40, which is available from Croda. Inc., and SA90HCO, which is $C_{18}H_{37}$—

$CH_2(CON(CH_3)CH_2(CHOH)_4CH_2OH)_2$. Surface modifiers which have been found to be particularly useful include Tetronic 908. the Tweens. Pluronic F-68 and polyvinylpyrrolidone. Other useful surface modifiers include:

decanoyl-N-methylglucamide;
n-decyl β-D-glucopyranoside;
n-decyl β-D-maltopyranoside;
n-dodecyl β-D-glucopyranoside;
n-dodecyl β-D-maltoside;
heptanoyl-N-methylglucamide;
n-heptyl-β-D-glucopyranoside;
n-heptyl β-D-thioglucoside n-hexyl β-glucopyranoside;
nonanoyl-N-methylglucamide;
n-noyl-β-D-glucopyranoside;
octanoyl-N-methylglucamide;
n-octyl-β-D-glucopyranoside;
octyl β-D-thioglucopyranoside; and the like.

Another useful surface modifier is tyloxapol (a nonionic liquid polymer of the alkyl aryl polyether alcohol type: also known as superinone or triton). This surface modifier is commercially available and/or can be prepared by techniques known in the art.

Another preferred surface modifier is p-isononylphenoxy-poly(glycidol) also known as Olin-10G or Surfactant 10-G, is commercially available as 10G from Olin Chemicals, Stamford, Conn.

One preferred surface modifier is a block copolymers linked to at least one anionic group. The polymers contain at least one, and preferably two, three, four or more anionic groups per molecule. Preferred anionic groups include sulfate, sulfonate, phosphonate, phosphate and carboxylate groups. The anionic groups are covalently attached to the nonionic block copolymer. The nonionic sulfated polymeric surfactant has a molecular weight of 1,000–50,000, preferably 2,000–40,000 and more preferably 3,000–30,000. In preferred embodiments the polymer comprises at least about 50%, and more preferably, at least about 60% by weight of hydrophilic units, e.g., alkylene oxide units. The reason for this is that the presence of a major weight proportion of hydrophilic units confers aqueous solubility to the polymer.

A preferred class of block copolymers useful as surface modifiers herein includes sulfated block copolymers of ethylene oxide and propylene oxide. These block copolymers in an unsulfated form are commercially available as Pluronics. Specific examples of the unsulfated block copolymers include F68, F108 and F127.

Another preferred class of block copolymers useful herein include tetrafunctional block copolymers derived from sequential addition of ethylene oxide and propylene oxide to ethylene diamine. These polymers in an unsulfated form, are commercially available as Tetronics.

The following investigation of preparing nanoparticle dispersions in non-aqueous media was completed for the elastase inhibitor WIN 63394. Oleic acid and three pharmaceutically acceptable oils, soybean oil, corn oil, and safflower seed oil were screened, with and without the addition of secondary stabilizers. Each combination was qualitatively characterized using light microscopy.

Favorable particle size reduction and particle dispersion stability were observed for WIN 63394 nanosuspensions milled with a Pluronic F127 to water ratio of 1:9 in oleic acid. Analysis of dispersions was limited by the their highly viscous nature. Dilution of soybean, corn, and safflower seed oil dispersions stabilized with Pluronic F127 to improve contrast between milled particles and the aqueos and non-aqueous was not effective. A description of the methods and procedures used for media conditioning, product recovery and qualitative microscopic analysis are discussed below.

All experiments requiring milling were completed in a dispersion mill. A 25 ml volume of dispersion was milled using 42.0 g of 0.5 mm acid washed glass beads. At the conclusion of the milling period, vacuum filtration was used to recover the product dispersion.

A Leitz Diaplan microscope with a PL Fluotar 100/1.32 oil object was used to make qualitative observations of the nanoparticle suspension character and estimate particle size of the product dispersions. Particle size distributions could not be quantitatively determined for dispersions in complex media such as oleic acid or oil, using traditional light scattering measurement methods, such as the Microtrac UPA, due to the viscosity and the refractive characteristics of the samples. A Sony color video camera printer was fitted to the microscope and allowed a hard copy micrograph of each sample to be generated for future reference.

The resolution of sample was limited due to the microscope power and the sample character. Dilution of each dispersion was completed using the respective oleic acid or oil medium to improve the contrast between particles and emulsion droplets. Dispersions milled in oleic acid/oil were diluted 1:2 in oleic acid/oil, respectively. This technique increased the resolution of the drug particles for dispersions milled in oleic acid. However, those suspensions milled in mils were unable to be diluted.

EXAMPLE 1

Eight stabilizer systems were screened to identify a potential stabilizer for milling WIN 63394 in oleic acid and was milled four hours. Each nanoparticulate dispersion contained 222.5 mg of WIN 63394 (1%) in a measured amount of stabilizer in 22.25 g oleic acid with 42.0 g of 0.5 mm acid washed glass beads. Table I outlines materials and stabilizers used to mill WIN 63394 in oleic acid.

TABLE I

| Material | Grade | Source |
|---|---|---|
| WIN 63394 | — | Sterling-Winthrop |
| Oleic Acid | NF | Spectrum |
| Stabilizer | | |
| Tween 80 | Reagent | Sigma |
| SPAN 80 | Reagent | ICI |
| Tyloxapol | Reagent | Sigma |
| Pluronic F68 | NF | BASF |
| Pluronic F127 | NF | BASF |
| Pluronic L122 | NF | BASF |
| Propylene glycol | Reagent | Aldrich |

A description of the trials completed using Example 1 stabilizers and the micrographs for each nanosuspension is found in Table II.

TABLE II

| Description of WIN 63394 Dispersions Milled In Oleic Acid | | |
|---|---|---|
| Trial | Stabilizer | Amount (% Total) |
| 1 | Tween 80 | 0.25 ml Tween 80 (1.0%) |

TABLE II-continued

Description of WIN 63394 Dispersions Milled In Oleic Acid

| Trial | Stabilizer | Amount (% Total) |
|---|---|---|
| 2 | SPAN 80 | 0.25 ml SPAN 80 (1.0%) |
| 3 | Tyloxapol | 0.25 ml Tyloxapol (1.0%) |
| 4 | $H_2O$<br>Pluronic F68 | 1.25 ml $H_2O$ (5.0%)<br>250 mg F68 (1.0%) |
| 5 | $H_2O$<br>Pluronic L122 | 1.25 ml $H_2O$ (5.0%)<br>250 mg L122 (1.0%) |
| 6 | $H_2O$<br>Pluronic F127 | 1.25 ml $H_2O$ (5.0%)<br>250 mg F127 (1.0%) |
| 7 | Propylene glycol | 6.25 ml (25%) |
| 8 | 50% NaOH solution | 12.5 ul (0.2%) |
| 9 | $H_2O$<br>Pluronic F127 | 1.25 ml $H_2O$ (5.0%)<br>250 mg F127 (1.0%) |

*Trial 9 was milled without WIN 63394 as a control for Trial 6.

In Table II, trials 1–8, WIN 63394 was milled in oleic acid at low solids concentrations. Trial 9 was used as a control for trial 6, which showed favorable particle size reduction of less than 1000 nanometers and good particle dispersion. In trial 8 WIN 63394 was milled without stabilizer for 3 hours and 12.5 µl 50% NaOH solution was added at 3 hours and milled for the final hour.

Good particle size reduction and stability observed in trial 6. That is, 5% $H_2O$, 1% Pluronic F127 in oleic acid. In all other trials, 1–5, 7 and 8, agglomeration of drug substance was observed. The stabilizer system of Pluronic F127 in water and oleic acid and increased WIN 63394 concentrations was investigated in Example 2.

EXAMPLE 2

Trials 10–12 were completed using solid stock Pluronic F127. A 10% Pluronic F127 solution was added to trial 13. Trials 14 and 15 were milled in oleic acid as controls for trial 13, trial 14 was milled without WIN 63394 and trial 15 was milled without the addition of Pluronic F127-H2O stabilizer. A description of the trials completed are found in Table III.

TABLE III

Description of WIN 63394 Dispersions Milled in Oleic Acid at Increased Solids Concentration

| Trial | % WIN 63394 | Stabilizer (F127:H₂O Ratio) | Water | Oleic Acid |
|---|---|---|---|---|
| 10 | 10.0% | 0.75 g F127 (dry) (1:5) | 15.0% | 18.6 ml |
| 11 | 15.0% | 0.75 g F127 (dry) (1:5) | 15.0% | 17.5 ml |
| 12 | 20.0% | 1.0 g F127 (dry) (1:5) | 20.0% | 15.0 ml |
| 13 | 10.0% | 7.5 ml–10% F127 soln (1:9) | — | 15.0 ml |
| 14 | — | 7.5ml–10% F127 soln (1:9) | — | 17.5 ml |
| 15 | 10.0% | — | — | 22.5 ml |

The results of experiments described in Example 2 revealed that at increased solid concentrations, i.e. 20%, dispersion viscosity is increased. As a result, milling efficiency was significantly reduced and the temperature of the suspension during milling increased dramatically. Trial 12 was discontinued after 30 minutes for these reasons. Comparison of Trials 13 and 14 is difficult due to the resolution of the samples. However, minimal agglomeration is observed in Trial 13 when diluted in 2 parts oleic acid. Trial 15 shows significant hard agglomeration in both diluted and undiluted samples.

EXAMPLE 3

In addition to the dispersions milled in oleic acid, an investigation of soybean, corn, and safflower seed oil was conducted. Again, dispersions were milled using 42 g of 0.5 mm acid washed glass beads as the milling agent. Table IV lists the materials used for these oil milling Trials.

TABLE IV

Materials Used for Screening of Milling Oil Medium

| Materials | Grade | Source |
|---|---|---|
| WIN 63394 | — | — |
| Soybean Oil | Reagent | Sigma |
| Corn Oil | Reagent | Sigma |
| Safflower Seed Oil | Reagent | Sigma |

Based on the favorable results in Trial 6, 5% $H_2O$–1% Pluronic F127 in oleic acid, 7.5 ml–10% Pluronic F127 solution was added to each oil medium. Controlled dispersions without stabilizer. Trials 16–18, and dispersions with stabilizer and without WIN 63394, trials 20, 22 and 24, were completed to distinguish between drug particles and other components of the emulsion suspension. A description of WIN 63394 dispersions milled in oil mediums with Pluronic F127 is found in Table V.

TABLE V

Description of WIN 63394 Dispersions Milled in Oil Mediums

| Trial | Stabilizer | % WIN 63394 | Medium/Amount [ml] |
|---|---|---|---|
| 16 | — | 3.0% | Soybean oil/ 24.25 ml |
| 17 | — | 3.0% | Corn oil/ 24.25 ml |
| 18 | — | 3.0% | Safflower seed oil/ 24.25 ml |
| 19 | 7.5 ml–10% F127 | 3.0 | Soybean oil/ 16.75 ml |
| 20 | 7.5 ml–10% F127 | — | Soybean oil/ 16.75 ml |
| 21 | 7.5 ml–10% F127 | 3.0% | Corn oil/ 16.75 ml |
| 22 | 7.5 ml–10% F127 | — | Corn oil/ 16.75 ml |
| 23 | 7.5 ml–10% F127 | 3.0% | Safflower seed oil/ 16.75 ml |
| 24 | 7.5 ml–10% F127 | — | Safflower seed oil/ 16.75 ml |

Micrographs of the diluted samples from Trials 16–18 showed minimal particle agglomeration. However, as was observed in micrographs of the samples in oleic acid, resolution in between the components in the dispersion was limited. Samples from the trials milled at low solids concentrations, Trials 19, 21 and 23 were observed to have the particles residing within large water droplets. Control Trials 20 and 22 formed stable emulsions while interconnected water droplets were observed in Trial 24. All attempts to dilute the samples in their respective oil medium were unsuccessful.

EXAMPLE 4

An attempt was made to optimize the Pluronic F127 to water ratio which provides a stable emulsion in oleic acid. The results of this evaluation are described below. Pluronic F127 and water were combined with 10 ml of oleic acid in 20 ml borosilicate glass vials. The vials were placed on a shaker for one hour at 400 rpm at 37 C. Qualitative analysis was completed using photomicroscopy to assess physical stability of each emulsion suspension immediately after shaking and after setting on a bench top for 3 days at 25° C. The conditions of the trialsare listed in Table IV.

TABLE VI

Description of Pluronic F127/H$_2$O Optimization Trials

| Trial | Stabilizer (F127:H$_2$O Ratio) | Water | Oleic Acid |
|---|---|---|---|
| 1 | 1 ml–1.0% F127 soln (1:200) | — | 10 ml |
| 2 | 1 ml–1.0% F127 soln (1:100) | — | 10 ml |
| 3 | 1 ml–5.0% F127 soln (1:20) | — | 10 ml |
| 4 | 1 ml–10% F127 soln (1:10) | — | 10 ml |
| 5 | 10 mg F127 (dry) (1:100) | 1 ml | 10 ml |
| 6 | 50 mg F127 (dry) (1:20) | 1 ml | 10 ml |
| 7 | 100 mg F127 (dry) (1:10) | 1 ml | 10 ml |
| 8 | 1 ml–0.5% F68 soln (1:200) | — | 10 ml |
| 9 | 1 ml–0.5% F68 soln (1:20) | — | 10 ml |

Trials 1–4 of Example 4 resulted in milky emulsions after shaking. Trials 5–7, which introduced the Pluronic F127 as a dry material also appeared to be well dispersed upon shaking, however the micrographs revealed undissolved F127 material dispersed in the oleic acid. Trials 1–7 separated into 3 phases after 3 days, but were easily returned to a milky emulsion with gentle agitation. Large water droplets were observed in the samples from Trials 8 and 9 after shaking. After 3 days, the emulsion separated into two phases and was difficult to return to an emulsion.

The results of Example 4 demonstrate that it is possible to produce a nanoparticulate aqueous dispersion emulsified in a continuous oil or fatty acid phase. Oleic acid as the fatty acid showed the best results; however, it is anticipated that other fatty acids would also produce stable nanoparticle aqueous dispersion emulsions.

The invention has been described in detail with particular reference to the preferred embodiments thereof, but it will be understood that variations and modifications can be affected within the spirit and scope of the invention.

What is claimed is:

1. Particles consisting essentially of 0.1–50.0% by weight of a crystalline drug substance having a solubility in water of less than 10.0 mg/ml, said crystalline drug substance having a non-cross-linked modifier adsorbed on the surface thereof in an amount of 0.1–20% by weight, said particles suspended in an aqueous phase, the aqueous phase emulsified in oleic acid, sufficient to maintain an effective particle size of less than 1000 nanometers.

2. The particles according to claim 1 wherein the surface modifier is poloxamers and water.

3. The particles according to claim 1 wherein the surface modifier is poloxamers.

* * * * *